United States Patent
Steuerwald et al.

(10) Patent No.: US 7,372,572 B2
(45) Date of Patent: May 13, 2008

(54) DEVICE FOR PHOTOMETRICALLY MEASURING THE CONCENTRATION OF A CHEMICAL SUBSTANCE IN A SOLUTION TO BE MEASURED

(75) Inventors: Ralf Steuerwald, Welzheim (DE); Matthias Knoedler, Fellbach (DE)

(73) Assignee: Endress + Hauser Conducta Gesellschaft fur Mess- u. Regeltechnik mbH + Co. KG, Gerlingen (DE)

( * ) Notice: Subject to any disclaimer, the term of this patent is extended or adjusted under 35 U.S.C. 154(b) by 0 days.

(21) Appl. No.: 10/552,724

(22) PCT Filed: Apr. 8, 2004

(86) PCT No.: PCT/EP2004/003826

§ 371 (c)(1),
(2), (4) Date: Jul. 26, 2006

(87) PCT Pub. No.: WO2004/090513

PCT Pub. Date: Oct. 21, 2004

(65) Prior Publication Data

US 2006/0263253 A1  Nov. 23, 2006

(30) Foreign Application Priority Data

Apr. 10, 2003  (DE)  ................ 103 16 685

(51) Int. Cl.
*G01N 21/00* (2006.01)
(52) U.S. Cl. ............ 356/436; 356/244; 356/433; 356/338; 422/82.05; 422/82.09
(58) Field of Classification Search ........ 356/244–246, 356/432, 433, 436, 338; 422/82.05–82.09
See application file for complete search history.

(56) References Cited

U.S. PATENT DOCUMENTS 5,272,345 A * 12/1993 Durham et al. ............. 356/436
6,046,804 A *  4/2000 Kawamura et al. ......... 356/246

FOREIGN PATENT DOCUMENTS

| DE | 25 53 565 A1 | 6/1977 |
| DE | 26 35 171 | 2/1978 |
| DE | 31 49 869 A1 | 6/1983 |
| DE | 35 10 052 A1 | 9/1986 |
| DE | 100 20 615 A1 | 11/2001 |

* cited by examiner

*Primary Examiner*—Layla G. Lauchman
*Assistant Examiner*—Iyabo S Alli
(74) *Attorney, Agent, or Firm*—Bacon & Thoms, PLLC

(57) ABSTRACT

An apparatus for photometric measurement of the concentration of a chemical substance in a solution, wherein a cuvette is provided containing the solution The cuvette is transmissive at least in predetermined regions for electromagnetic radiation, wherein a transmitting unit is provided, which produces electromagnetic radiation in at least two wavelength regions and which radiates into the cuvette The electromagnetic radiation in a first wavelength region serves for measurement purposes and the electromagnetic radiation in a second wavelength region is used for reference purposes The electromagnetic radiation in the two wavelength regions takes the same path through the cuvette and through the solution At least one detector unit is provided, which is so arranged that it receives the electromagnetic radiation in the at least two wavelength regions following passage through the solution, and wherein a control/evaluation unit is provided, which determines the concentration of at least one chemical substance in the solution on the basis of the electromagnetic radiation detected in the two wavelength regions.

14 Claims, 2 Drawing Sheets

DEVICE FOR PHOTOMETRICALLY MEASURING THE CONCENTRATION OF A CHEMICAL SUBSTANCE IN A SOLUTION TO BE MEASURED

FIELD OF THE INVENTION

The invention relates to an apparatus for the photometric measurement of concentration of at least one chemical substance in a solution. The solution can be an aqueous solution or a suspension. In principle, the invention can be used for detecting any dissolved substance, which is detectable via a photometric measuring method. Wet chemically, e.g. the following substances can be determined: Aluminum, ammonium, calcium, chlorine, chromium, iron, hydrazine, manganese, nitrate, nitrite, phosphate, silicate and sulfide. Likewise, the hardness of an aqueous solution can be determined. The manner in which a photometer works rests on the Lambert-Beer law.

BACKGROUND OF THE INVENTION

Known online systems for nitrate measurement or for measuring the content of organic substances are also available from Endress+Hauser under the mark STAMOSENS.

DE 199 02 396 C2 discloses an arrangement for measuring the nitrate content of liquids. In the case of this known arrangement, the radiation from a UV light source is split via two crossed, deflecting mirrors into parts traveling on two measurement branches in a measuring cuvette. One branch is for UV radiation reception and the other branch is for IR radiation reception. By measuring the nitrate concentration in the maximum (preferably at 214 nm) and in the minimum (preferably at 830 nm) of the nitrate absorption curve, a high measuring accuracy is achieved, since the arrangement of the two measuring branches with different wave lengths (two channel system) makes possible, in simple manner, the mathematical compensation of disturbing influences, such as clouding substances, aging effects of the light source and foulings of the cuvette.

In the case of known photometric measuring equipment, depending on the substance to be measured, either a wavelength-specific LED or a broadband light source is used. In the case of the broadband light source, the selection of the required wavelength is accomplished by an interference filter, which is arranged either after the light source or in front of the detector unit. The detector unit can be at least one photodiode, phototransistor or similar photoelectric component.

SUMMARY OF THE INVENTION

An object of the invention is to provide an apparatus, with which the effectiveness of the compensation of interferences can be improved.

The object is achieved by an apparatus which includes the following components:
- a cuvette, for receiving a solution to be measured, with the cuvette being transmissive for electromagnetic radiation at least in predetermined regions;
- a transmitting unit, which generates electromagnetic radiation in at least two wavelength regions and which radiates into the cuvette, with the electromagnetic radiation in a first wavelength region serving for measuring purposes and the electromagnetic radiation in a second wavelength region being used for reference purposes, and with the electromagnetic radiation in both wavelength regions taking the same path through the cuvette and the solution;
- at least one detector unit, which is so arranged that it receives the electromagnetic radiation in the at least two wavelength regions after the radiation has passed through the solution;
- a control/evaluation unit, which, on the basis of the electromagnetic radiation detected in the two wavelength regions, determines the concentration of the chemical substance in the solution.

According to the invention, the radiation in the at least two required wavelength regions is provided from only one light source. This has the advantage that the path of the radiation through the cuvette and, as required, through the solution is identical for the concentration measurement and for the reference, or compensation, measurement. Especially in such case, clouding substances or foulings in the solution, and/or in and on the cuvette, influence the concentration measurement and the reference measurement in exactly the same manner. The control/evaluation unit, moreover, calculates the concentration of the substance in the solution preferably on the basis of the absorption of the radiation in the measuring branch and in the reference branch with the help of the Lambert-Beer law. In such case, the reference measurement serves for determining the beginning intensity $I_0$, while the concentration measurement is related to the intensity I of the radiation after passage through the solution.

Especially advantageous is the further development of the apparatus of the invention, in which the transmitting unit includes a two-color light-emitting diode. By way of example, LEDs with the following wavelengths are used for wet-chemical determinations: 660 nm and 880 nm, 565 nm and 880 nm, 430 nm and 565 nm, 660 nm and 565 nm, 660 nm and 430 nm, 502 nm and 880 nm, 810 nm and 565 nm, 810 nm and 430 nm, 525 nm and 880 nm, 555 nm and 880 nm. Of course, also other wavelength regions can be used for different applications. Also, instead of a two-color LED, also three-, or more-, color LEDs can be used. In such embodiments, it becomes possible to determine and/or monitor concentrations of plural substances in a solution.

In an advantageous further development of the apparatus of the invention, the essentially oppositely lying surfaces of the cuvette are transmissive for the electromagnetic radiation radiated from the transmitting unit. The oppositely lying surfaces can, for example, be the ends or the long sides of a tubular cuvette. The material of the cuvette can be, for example, glass or plastic. An advantageous embodiment is one in which the transmitting unit and/or the receiving unit are located in the region of the mutually opposing surfaces, e.g. the end surfaces or the long sides of the cuvette. An advantageous embodiment is that in which the transmitting unit and/or the receiving unit is/are arranged in the regions of the oppositely lying surfaces, or the ends or the long sides of the cuvette.

An advantageous embodiment of the apparatus of the invention provides an aperture between the transmitting unit and/or the detector unit, on the one hand, and, on the other hand, the cuvette surfaces, or ends, or long sides transmissive for the electromagnetic radiation. The aperture serves for the optical shading of the edge regions of the cuvette, where air bubbles like to cling rather easily and/or toward which air bubbles tend to migrate as they make their passage through the cuvette. Furthermore, it is advantageous, once a certain length of cuvette is reached, to arrange a lens between the light source and the facing, transmissive region of the cuvette, for the purpose of focussing the radiation. A lens is preferably used, when the optical path length is greater than 5 mm.

In an especially interesting and advantageous embodiment of the apparatus of the invention, an inlet is provided in a first end region of the cuvette and an outlet in a second end region of the cuvette, with the inner diameter of the outlet being greater than the inner diameter of the inlet. This embodiment effectively counteracts air bubble formation in the cuvette. This embodiment is preferably used, when the sample taking is from a pressure line. Thus, in the case of sample taking from a pressure line, the effect is amplified that air contained in the solution outgasses in the relatively large-volume cuvette. It has been found that air bubble formation in the cuvette is then already effectively prevented, when the inner diameter of the outlet is twice as large as the inner diameter of the inlet.

A preferred further development of the apparatus of the invention provides that at least the cuvette, with the inlet and the outlet, possibly also with the transmitting unit and the detector unit, are embodied as an integral measuring unit. The measuring unit with cuvette, inlet and outlet, possibly also with transmitting unit and detector unit, lies essentially in a plane. Either the inlet and the outlet can be arranged in an extension of the longitudinal axis of the cuvette, or the inlet and the outlet are arranged at right angles to the longitudinal axis of the cuvette. The longitudinal axis of the cuvette is, in such case, defined as the axis which lies in the flow direction of the solution through the cuvette.

Especially advantageous is the embodiment of the apparatus of the invention in which the measuring unit is oriented in the measurement position in such a manner relative to the horizontal plane, that the outlet end of the measuring unit lies higher than the inlet end of the measuring unit. Preferably, the plane, in which the measuring unit is arranged, is inclined at an angle between 5° and 45° relative to the horizontal plane. This assures that no undesired air volumes form in the cuvette to falsify the concentration measurements.

An alternative embodiment provides that the inlet is arranged at a first predetermined angle to the longitudinal axis of the cuvette and that the outlet is arranged at a second predetermined angle to the longitudinal axis of the cuvette. Especially in this embodiment, also the inner diameter of the outlet is again greater than the inner diameter of the inlet. However, it is also possible in the case of this embodiment, for the purpose of counteracting bubble formation, that the inner diameters of inlet and outlet are equal.

Additionally, it can be provided that at least one heating element is associated with the cuvette. The heating element can be a resistive heating element or a Peltier element, which is directly, or indirectly, in contact with the cuvette. The heating element enables changing of the rate of reaction in the solution.

BRIEF DESCRIPTION OF THE DRAWINGS

The invention will now be explained in greater detail on the basis of the drawings, the figures of which show as follows.

DESCRIPTION OF THE PREFERRED EMBODIMENTS

Figure 1:
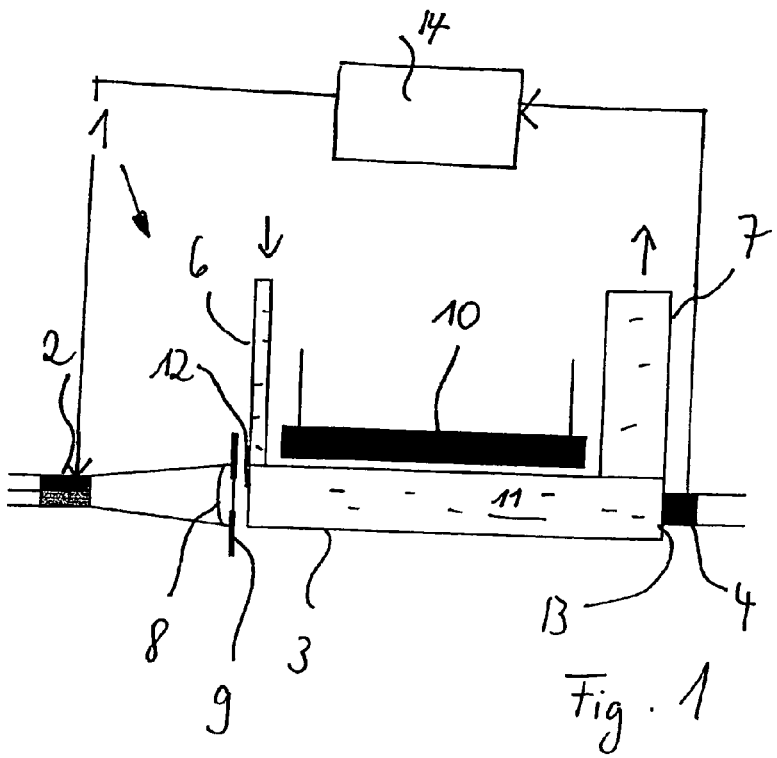
FIG. 1 a first advantageous form of embodiment of the apparatus of the invention.

FIG. 1 shows a first advantageous form of embodiment of the apparatus 1 of the invention. The transmitting unit 2 is a two-color LED. The two-color LED serves both for the concentration measurement and for the reference measurement. Since the path of the radiation through the solution 11 for concentration measuring purposes and for reference purposes is absolutely identical, the known interfering variables, such as a clouding of the solution 11, a fouling of the cuvette 3 or an aging effect of the transmitting unit 2, can be very effectively compensated. The two-color LED is controlled via the control/evaluation unit 14, in a manner such that it alternately emits the electromagnetic radiation in the two wavelength regions. The radiation of the two-color LED is focussed via lens 8. The use of a lens 8 for the purpose of focussing the measuring and reference radiation is always recommendable, when the optical path length of the cuvette 3 is greater than 5 mm. Additionally provided between lens 8 and the radiation-transmissive end-surface 12 of the cuvette 3 is an aperture 9. Aperture 9 serves for the optical shading of the edge regions of cuvette 3. This is important to the extent that air bubbles like to accumulate very easily in these edge regions, or to the extent that the air bubbles move through preferably in these edge regions.

In the illustrated case, the two oppositely lying end surfaces 12, 13 of the cuvette 3 are transmissive for the measuring radiation and for the reference radiation. The transmitting unit 2 is positioned at an end surface 12, while, at the oppositely lying end surface 13, the detector unit 4 is arranged. Detector unit 4 determines both the intensity of the measuring radiation and also the intensity of the reference radiation, following passage of the radiation through the solution 11. On the basis of the intensity measurements, the control/evaluation unit 14 determines the concentration of the substance to be measured in the solution 11. Preferably, the detector unit 4 is a broadband photodiode, which is capable of detecting the electromagnetic radiation in the different wavelength regions. Especially advantageous is the case in which the photodiode is associated with an electronic circuit. The electronic circuit converts the input to the logarithm thereof, so that a linear output signal is provided at the output of the electronic circuit, or the photodiode, as the case may be.

In the embodiment shown in FIG. 1, the inner diameters of inlet 6 and outlet 7 are dimensioned differently. The inner diameter of the outlet 7 is greater than the inner diameter of the inlet 6. In this way, small air bubbles in the solution 11 can easily escape. This is important in so far as small air bubbles in the solution 11 can significantly compromise the measurement accuracy. It has been found that escape of small air bubbles is already sufficiently assured, when the inner diameter of the outlet 7 is about twice as large as the inner diameter of the inlet 6.

Cuvette 3 can be made, for example, of glass or plastic. A heating element 10 is associated with cuvette 3. Especially, heating element 10 serves for lessening the reaction rate of the solution 11 being measured.

Figure 2:
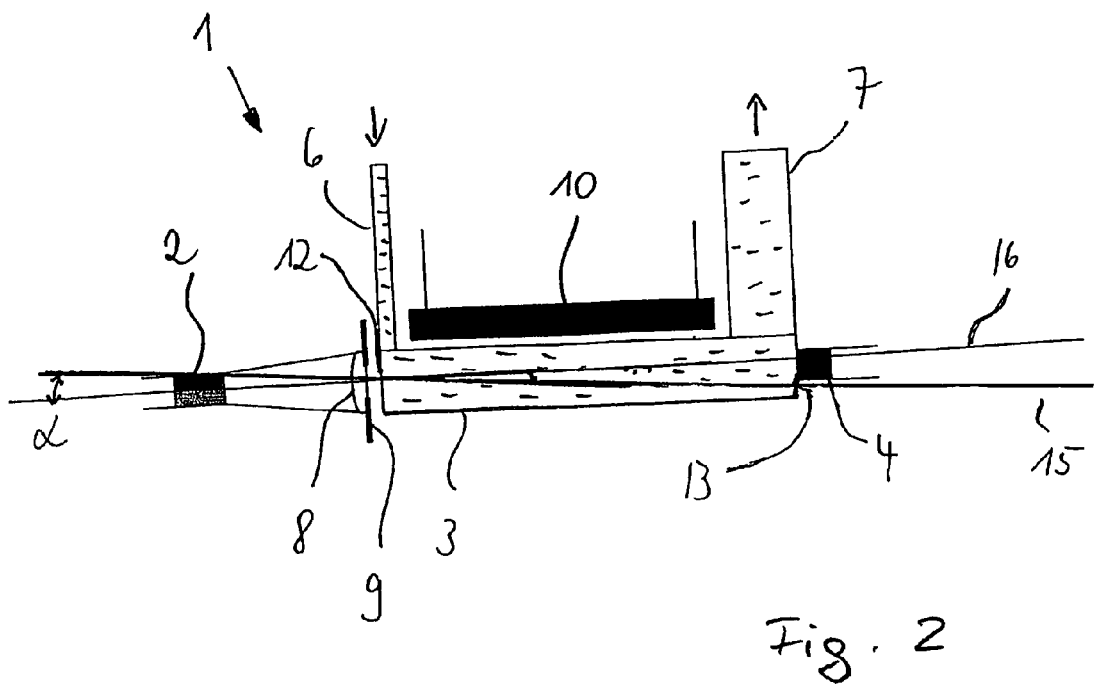
FIG. 2 a second advantageous form of embodiment of the apparatus of the invention.

FIG. 2 shows a second advantageous form of embodiment of the apparatus 1 of the invention. In this case, additional measures are introduced, which counteract the formation of small gas bubbles in the solution 11, or improve the escape of such bubbles from the solution, as the case may be. At least cuvette 3, with the inlet 6 and the outlet 7, the transmitting unit 2 and the detector unit 4, form a measuring unit. The measuring unit is so arranged, that the outlet 7 of the cuvette 3 lies higher than the inlet 6. The plane 16, in which the measuring unit is arranged, is thus inclined by an angle a relative to the horizontal plane 15. In this way, it is assured that the interior of the cuvette 3 is always filled completely with the solution 11 being measured.

Figure 3:
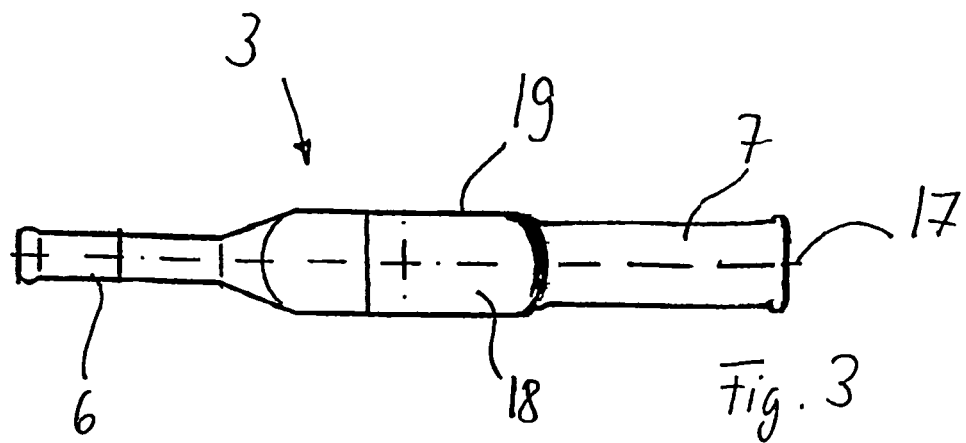
FIG. 3 a first embodiment of the cuvette.

FIG. 3 shows a cuvette 3 where the inlet 6 and the outlet 7 are located in the direction of the longitudinal axis 17. Also in the case of this embodiment of the cuvette 3, the outlet 7 has a greater inner diameter than the inlet. In order still more effectively to counteract bubble formation in the cuvette 3, also here, the outlet 7 can lie higher than the inlet 6.

Figures 4, 5:
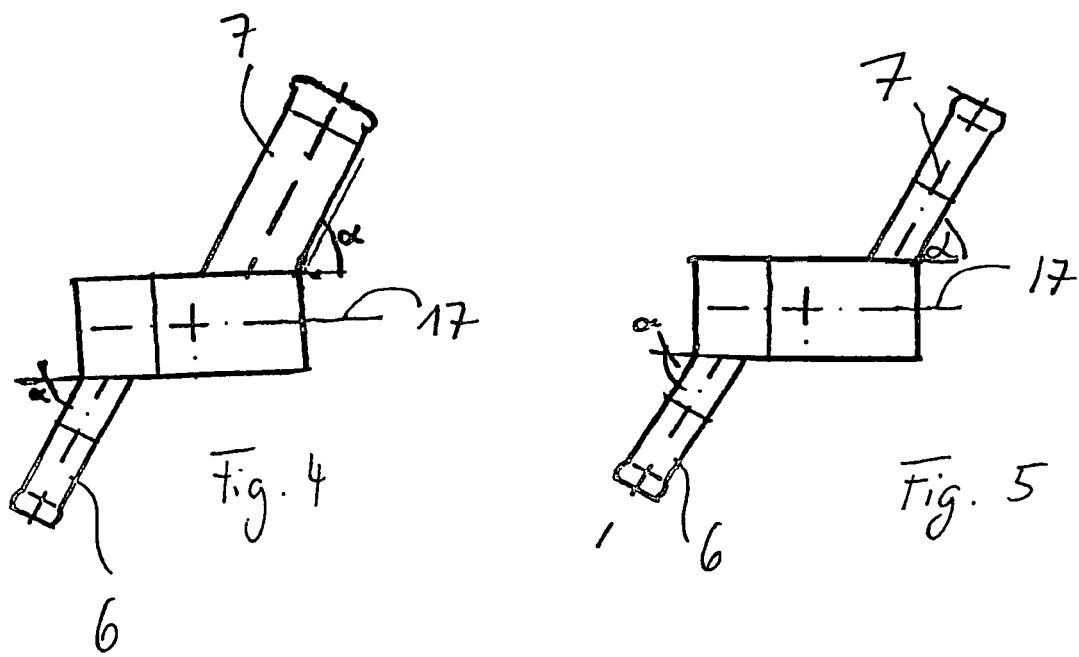
FIG. 4 a second embodiment of the cuvette.
FIG. 5 a third embodiment of the cuvette.
Figure 6:
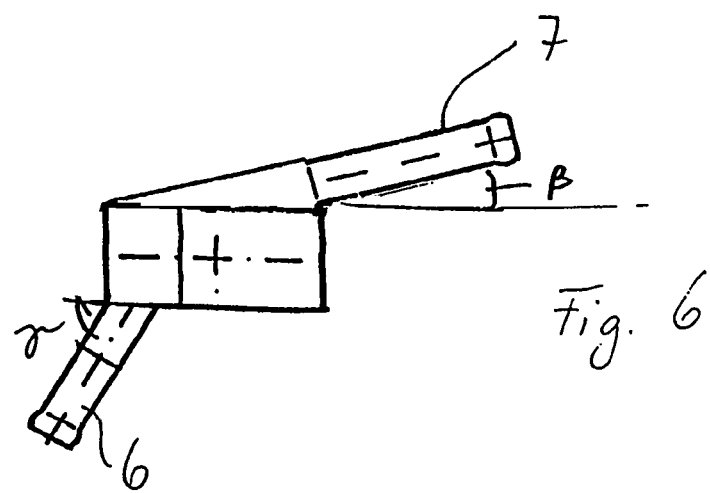
FIG. 6 a fourth embodiment of the cuvette.

An alternative embodiment to the arrangement shown in FIG. 2 with the inclined position of the measuring arrangement is shown in FIGS. 4 to 6. Here, inlet 6 and outlet 7 are arranged at a predetermined angle a to the longitudinal axis 17 of the cuvette 3. Either the inner diameters of inlet 6 and outlet 7 are dimensioned differently (FIG. 5, FIG. 7), or the inner diameters of inlet 6 and outlet 7 have the same dimensions (FIG. 5). Likewise, the angular arrangement of inlet 6 and outlet 7 can be the same (FIG. 4, FIG. 5) or different (FIG. 6).

The invention claimed is:

1. An apparatus for the photometric measurement of concentration of at least one chemical substance in a solution, comprising:
   a cuvette, for containing the solution, said cuvette being transmissive for electromagnetic radiation, at least in predetermined regions;
   a transmitting unit, which produces electromagnetic radiation in at least two wavelength regions and radiates into said cuvette, wherein the electromagnetic radiation in a first wavelength range serves for measuring purposes and wherein the electromagnetic radiation in a second wavelength region is used for reference purposes, and wherein the electromagnetic radiation in the two wavelength regions takes the same path through said cuvette and through the solution;
   at least one detector unit, which is so arranged that it receives the electromagnetic radiation in the at least two wavelength ranges following its passage through the solution; and
   a control/evaluation unit, which determines the concentration of the chemical substance in the solution on the basis of the electromagnetic radiation detected in the two wavelength regions, wherein:
   said control/evaluation unit controls said transmitting unit in a manner such that it alternately emits the electromagnetic radiation in said at least two wavelength regions.

2. The apparatus as claimed in claim 1, wherein:
   essentially oppositely lying surfaces of said cuvette are transmissive for the electromagnetic radiation radiated from said transmitting unit.

3. The apparatus as claimed in claim 2, wherein:
   said oppositely lying surfaces are ends or lateral surfaces of said cuvette, and said cuvette is tubular.

4. The apparatus as claimed in claim 2, wherein:
   said transmitting unit and/or said receiving unit is/are arranged in the region of the ends or the lateral surfaces of said cuvette.

5. The apparatus as claimed in claim 1, wherein:
   said transmitting unit is a multi-color, for instance a two-color, light emitting diode.

6. The apparatus as claimed in claim 1, wherein:
   an aperture is provided between said transmitting unit and/or said detector unit, on the one hand, and the surface transmissive for the electromagnetic radiation, e.g. end or lateral surface of said cuvette.

7. The apparatus as claimed in claim 1, wherein:
   an inlet is provided in a first end region of said cuvette, an outlet is provided in a second end region of said cuvette; and
   the inner diameter of said outlet is greater than the inner diameter of said inlet.

8. The apparatus as claimed in claim 1, wherein:
   said inlet and said outlet are arranged in extensions of the longitudinal axis of said cuvette, or wherein said inlet and said outlet of said cuvette are arranged essentially at right angles to the longitudinal axis of said cuvette.

9. The apparatus as claimed in claim 1, wherein:
   said inlet is arranged at a first predetermined angle to the longitudinal axis of said cuvette and wherein said outlet is arranged at a second predetermined angle to the longitudinal axis of said cuvette.

10. The apparatus as claimed in claim 1, wherein:
    at least said cuvette with said inlet and said outlet, and, optionally, said transmitting unit and said detector unit, are arranged as an integral measuring unit.

11. The apparatus as claimed in claim 1, wherein:
    said cuvette with said inlet and said outlet, said transmitting unit and said detector unit lie essentially in one plane.

12. The apparatus as claimed in claim 10, wherein:
    said measuring unit in the measuring position is inclined in such a manner relative to the horizontal plane, that said outlet of said measuring unit lies higher than said inlet of said measuring unit.

13. The apparatus as claimed in claim 12, wherein:
    the plane, in which said measuring unit is arranged, is inclined by an angle between 5° and 45° relative to the horizontal plane.

14. The apparatus as claimed in claim 1, further comprising:
    at least one heating element, via which the temperature of said cuvette is variable.

* * * * *